US008634627B2

(12) United States Patent
Fujisawa

(10) Patent No.: US 8,634,627 B2
(45) Date of Patent: Jan. 21, 2014

(54) IMAGE PROCESSING APPARATUS, X-RAY CT APPARATUS, AND IMAGE PROCESSING METHOD

(75) Inventor: Yasuko Fujisawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 119 days.

(21) Appl. No.: 13/424,818

(22) Filed: Mar. 20, 2012

(65) Prior Publication Data
US 2012/0243759 A1 Sep. 27, 2012

(30) Foreign Application Priority Data

Mar. 23, 2011 (JP) ................. 2011-064813

(51) Int. Cl.
G06K 9/00 (2006.01)
(52) U.S. Cl.
USPC ................. 382/131; 378/4; 128/922
(58) Field of Classification Search
USPC ............. 382/100, 128, 129, 130, 131, 132; 128/922; 378/4–27
See application file for complete search history.

(56) References Cited

U.S. PATENT DOCUMENTS

| 5,647,360 | A * | 7/1997 | Bani-Hashemi et al. ..... 600/425 |
| 7,248,726 | B2 * | 7/2007 | Sasada ........................ 382/132 |
| 7,292,720 | B2 * | 11/2007 | Horger et al. ................. 382/131 |
| 7,409,078 | B2 * | 8/2008 | Pescatore et al. ............. 382/130 |
| 7,505,549 | B2 * | 3/2009 | Ohishi et al. ..................... 378/4 |
| 7,660,384 | B2 * | 2/2010 | Partain et al. ................... 378/37 |
| 7,949,170 | B2 * | 5/2011 | Goto et al. .................... 382/131 |
| 7,953,263 | B2 * | 5/2011 | Okamoto et al. ............. 382/128 |
| 8,526,694 | B2 * | 9/2013 | Pajeau .......................... 382/130 |
| 2005/0111719 | A1 * | 5/2005 | Pescatore et al. ............. 382/130 |
| 2008/0037845 | A1 * | 2/2008 | Deuerling-Zheng et al. . 382/130 |

FOREIGN PATENT DOCUMENTS

JP 2009-225979 10/2009

* cited by examiner

Primary Examiner — Anand Bhatnagar
(74) Attorney, Agent, or Firm — Oblon, Spivak, McClelland, Maier & Neustadt, L.L.P.

(57) ABSTRACT

An image processing apparatus includes a contrast side obtaining unit, estimating unit, a simple side obtaining unit, a core area computing unit, a synthesizing unit and a display control unit. The contrast side obtaining unit obtains a contrast area and a high CT value area around the contrast area. The estimating unit estimates a contrast area in the non-contrast data and corresponding to the obtained contrast area. The simple side obtaining unit obtains a high CT value area around the estimated contrast area. The core area computing unit computes a core area included in the high CT value area of the contrast data and the non-contrast data. The synthesizing unit aligns the contrast data with the non-contrast data and generates superimposed data by superimposing the high CT value area of the contrast data on the non-contrast data. The display control unit displays the superimposed data on a display device.

19 Claims, 8 Drawing Sheets

IMAGE PROCESSING APPARATUS, X-RAY CT APPARATUS, AND IMAGE PROCESSING METHOD

CROSS-REFERENCE TO RELATED APPLICATION

This application is based upon and claims the benefit of priority from Japanese Patent Application No. 2011-64813, filed on Mar. 23, 2011, the entire contents of which are incorporated herein by reference.

FIELD

An embodiment described herein relates to an image processing apparatus, an X-ray CT (computed tomography) apparatus, and an image processing method for performing image-processing on CT data.

BACKGROUND

An X-ray CT apparatus provides information on a subject as an image on the basis of the strengths of the X-rays that have passed through the subject. The X-ray CT apparatuses play an important role in various medical practices such as diagnosis and treatment of a disease and operative planning.

A CT image, which is used as a diagnostic image, obtained by an X-ray CT apparatus may, in some cases, include a group of pixels having a high CT value (a high CT value area) with halation, such as a calcified or a stent (metal) area. A CT image including a high CT area cannot provide an accurate evaluation of a lumen of a blood vessel. As an approach to accurately evaluate a lumen of a blood vessel, there is a method for generating a subtraction image as a diagnostic image by performing subtraction processing in order to delete a high CT value area from a diagnostic image. A simple CT image including a high CT value area and a contrast CT image including a high CT value area obtained by an X-ray CT apparatus are used to perform subtraction processing between both the images.

However, according to the conventional technique, burring may be found in a high CT value area occurring in each of a simple CT image and a contrast CT image due to positional deviations caused by cardiac movements and a cardiac phase difference (respiratory movements). In addition, generally, since a simple CT image has no reference information that can be used for alignment (i.e. much less CT value distribution representative of a characteristic feature is available than a contrast CT image), a method that uses normalized mutual information (NMI) of a simple CT image and a contrast CT image as similarity and a non-linear alignment based on anatomical information are both inaccurate.

Unfortunately, subtraction processing between a simple CT image and a contrast CT image in accordance with the conventional technique may leave a false image of a high CT value area caused by blurring on a subtraction image.

BRIEF DESCRIPTION OF THE DRAWINGS

In accompanying drawings.

DETAILED DESCRIPTION

Figure 1:
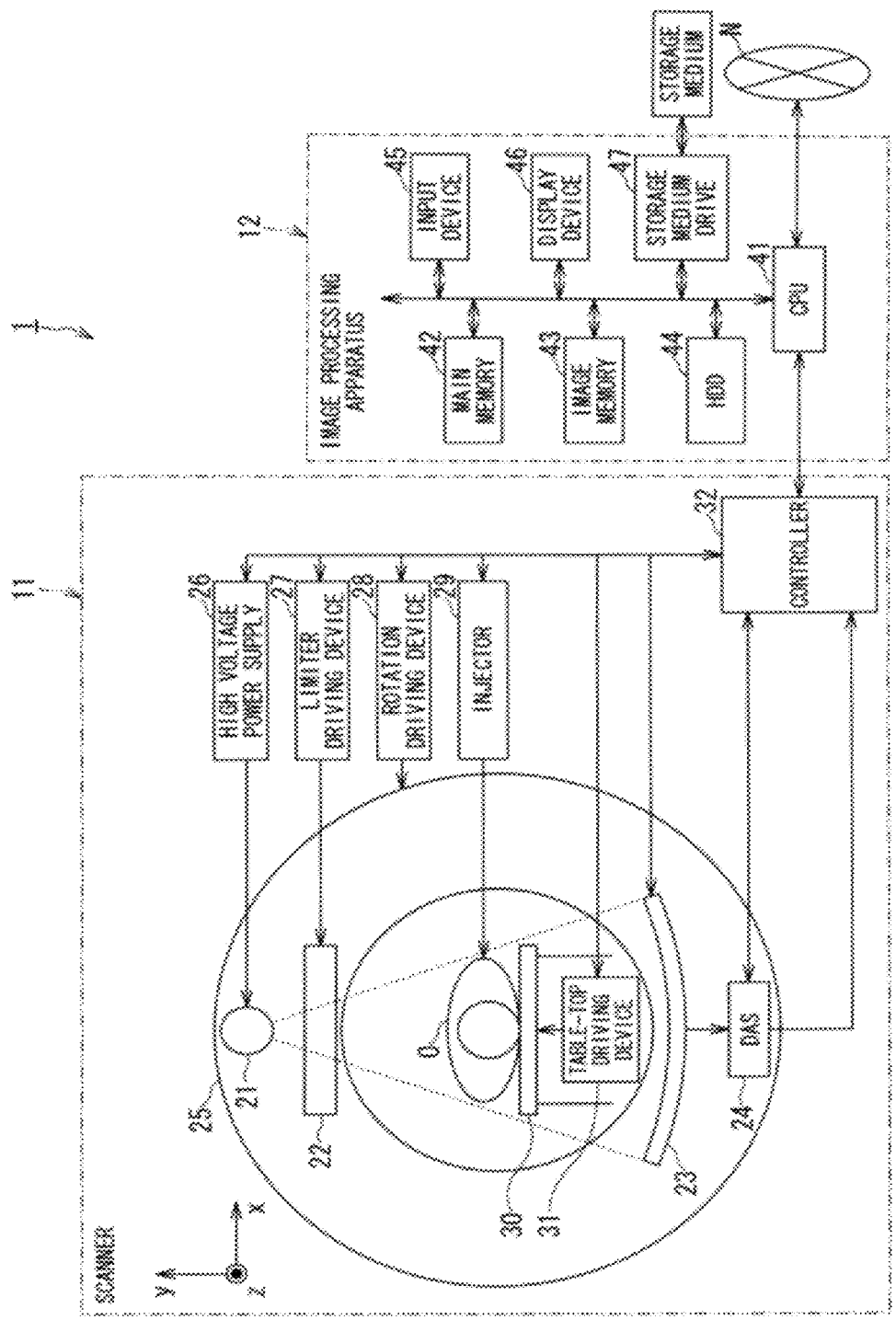
FIG. 1 is a hardware block diagram illustrating an X-ray CT apparatus according to a present embodiment.

An image processing apparatus, an X-ray CT apparatus, and an image processing method of a present embodiment will be described with reference to the accompanying drawings.

To solve the above-described problems, the image processing apparatus according to the present embodiment includes: a contrast side obtaining unit configured to, on the basis of contrast data obtained after contrast radiography is performed, obtain a contrast area and a high computed tomography (CT) value area around the contrast area; an estimating unit configured to, on the basis of the contrast data and aligned non-contrast data obtained without contrast, estimate a contrast area in the non-contrast data and corresponding to the obtained contrast area; a simple side obtaining unit configured to obtain a high CT value area around the estimated contrast area on the basis of the non-contrast data; a core area computing unit configured to, on the basis of a distribution of CT values of the contrast data, compute a core area included in the high CT value area of the contrast data and to, on the basis of a distribution of CT values of the non-contrast data, compute a core area included in the high CT value area of the non-contrast data; a synthesizing unit configured to, on the basis of the core area of the contrast data and the core area of the non-contrast data, align the contrast data with the non-contrast data and generate superimposed data by superimposing the high CT value area of the contrast data on the non-contrast data; and a display control unit configured to display the superimposed data on a display device.

Further, to solve the above-described problems, the image processing apparatus according to the present embodiment includes: an extracting unit configured to, on the basis of a blood vessel area of non-contrast image data, extract an object area in which an object exists; an estimating unit configured to, on the basis of the object area in the non-contrast image data, estimate pixel values or correction values of the pixel values of a corresponding area of the object area, in contrast image data; and a subtracting unit configured to perform subtraction processing between the non-contrast image data and the contrast image data to generate subtraction image data and to determine pixel values of an area corresponding to the corresponding area, in the subtraction image data, by using the estimated pixel values or correction values of the corresponding area.

To solve the above-described problems, the X-ray CT apparatus according to the present embodiment includes: a scanning unit configured to generate contrast data obtained after contrast radiography and non-contrast data obtained without contrast by controlling an X-ray source and an X-ray detector; a contrast side obtaining unit configured to, on the basis of the contrast data, obtain a contrast area and a high CT value area around the contrast area; an estimating unit configured to, on the basis of the contrast data and aligned non-contrast data, estimate a contrast area in the non-contrast data and corresponding to the obtained contrast area; a simple side obtaining unit configured to obtain a high CT value area around the estimated contrast area on the basis of the non-contrast data; a core area computing unit configured to, on the basis of a distribution of CT values of the contrast data, compute a core area included in the high CT value area of the contrast data and to, on the basis of a distribution of CT values of the non-contrast data, compute a core area included in the high CT value area of the non-contrast data; a synthesizing unit configured to, on the basis of the core area of the contrast data and the core area of the non-contrast data, align the contrast data with the non-contrast data and generate superimposed data by superimposing the high CT value area of the contrast data on the non-contrast data; and a display control unit configured to display the superimposed data on a display device.

To solve the above-described problems, the image processing method according to the present embodiment includes: obtaining a contrast area and a high CT value area around the contrast area on the basis of contrast data stored in a storage and obtained after contrast radiography is performed; estimating a contrast area in non-contrast data stored in a storage and obtained without contrast, and corresponding to the obtained contrast area on the basis of the contrast data and aligned non-contrast data; obtaining a high CT value area around the estimated contrast area on the basis of the non-contrast data; computing a core area included in the high CT value area of the contrast data on the basis of a distribution of CT values of the contrast data, and computing a core area included in the high CT value area of the non-contrast data on the basis of a distribution of CT values of the non-contrast data; aligning the contrast data with the non-contrast data on the basis of the core area of the contrast data and the core area of the non-contrast data, and generating superimposed data by superimposing the high CT value area of the contrast data on the non-contrast data; and displaying the superimposed data on a display device.

The X-ray CT apparatus of the present embodiment includes various types such as a rotation/rotation type in which an X-ray source and an X-ray detector simultaneously rotate around a subject and a stationary/rotation type in which a large number of detecting elements are arrayed in a ring shape and only an X-ray source rotates around a subject. Any type can be applied to the present invention. Herein, the rotation/rotation type, which is in the mainstream, will be described.

The dominating mechanism for converting incident X-rays into electrical charge includes indirect conversion in which X-rays are converted into light with a fluorescent substance such as a scintillator and the light is further converted into electrical charge by a photoelectric transducer such as a photodiode and direct conversion which uses generation of electron-hole pairs in a semiconductor by X-rays and their migration to an electrode, that is, a photoconductive phenomenon.

Additionally, what is called multi-tubular X-ray CT apparatuses in which a plurality of pairs of an X-ray source and an X-ray detector are mounted on a rotation ring have become commercially available in recent years, and related techniques of the multi-tubular X-ray CT apparatuses have been developed. The X-ray CT apparatus of the present embodiment may be applied to any of the conventional single-tubular X-ray CT apparatuses and the multi-tubular X-ray CT apparatuses. Herein, a single-tubular X-ray CT apparatus will be described.

FIG. 1 is a hardware block diagram illustrating the X-ray CT apparatus according to the present embodiment.

FIG. 1 illustrates an X-ray CT apparatus 1 of the present embodiment. The X-ray CT apparatus 1 is generally composed of a scanner 11 and an image processing apparatus 12. The scanner 11 of the X-ray CT apparatus 1 is typically installed in an examination room and a patient (subject) O and generates X-ray transmission data of a region with beating (a blood vessel, a coronary artery, a carotid artery, an aorta, etc.). On the other hand, the image processing apparatus 12 is typically installed in a control room adjacent to the examination room and generates projection data on the basis of the transmission data to generate and display a reconstruction image.

The scanner 11 of the X-ray CT apparatus 1 includes an X-ray tube (X-ray source) 21, an X-ray aperture limiter 22, an X-ray detector 23, a DAS (data acquisition system) 24, a rotation portion 25, a high voltage power supply 26, a limiter driving device 27, a rotation driving device 28, an injector (contrast medium injecting apparatus) 29, a table-top 30, a table-top driving device 31, and a controller 32.

The X-ray tube 21 causes an electron beam to collide with a metal target in accordance with tube voltage supplied from the high voltage power supply 26 to generate X-rays, and applies the X-rays to the X-ray detector 23. The X-rays applied from the X-ray tube 21 form fan beam X-rays and cone beam X-rays. Controlled by the controller 32 through the high voltage power supply 26, the X-ray tube 21 is supplied with power required to apply X-rays.

The limiter driving device 27 causes the X-ray aperture limiter 22 to adjust an area irradiated by the X-ray tube 21 with X-rays in a slice direction. That is, the limiter driving device 27 adjusts an aperture by the X-ray aperture limiter 22 to enable the area irradiated with X-rays in the slice direction to be changed.

The X-ray detector 23 is a matrix-formed X-ray detector, that is, the X-ray detector 23 is a two-dimensional array type X-ray detector (also referred to as a multi-slice type detector) having a plurality of channels in a channel direction and a plurality of rows of X-ray detecting elements in the slice direction. The X-ray detecting elements of the X-ray detector 23 detect the X-rays applied from the X-ray tube 21.

The DAS 24 amplifies a signal of transmission data detected by each X-ray detecting element of the X-ray detector 23 to convert the signal into a digital signal. Output data of the DAS 24 is supplied to the image processing apparatus 12 through the controller 32 of the scanner 11.

The rotation portion 25 holds the X-ray tube 21, the X-ray aperture limiter 22, the X-ray detector 23, and the DAS 24 as a single unit. The rotation portion 25 can rotate about the patient O with the X-ray tube 21, the X-ray aperture limiter 22, the X-ray detector 23, and the DAS 24 as a single unit and with the X-ray tube 21 and the X-ray detector 23 opposing each other. It is assumed that a direction parallel to an axis of rotation of the rotation portion 25 is defined as a z-axis direction, and a plane orthogonal to the z-axis direction is defined as an x-axis direction and a y-axis direction.

Controlled by the controller 32, the high voltage power supply 26 supplies the X-ray tube 21 with power required to apply X-rays.

The limiter driving device 27 has a mechanism that, controlled by the controller 32, adjusts an area to be irradiated with X-rays in the slice direction at the X-ray aperture limiter 22.

The rotation driving device 28 has a mechanism that, controlled by the controller 32, causes the rotation portion 25 to rotate about a cavity space with a positional relationship of the rotation portion 25 maintained.

The injector 29 is an apparatus that, controlled by the controller 32, injects a contrast medium into a catheter (a catheter tube, not shown) that is inserted in an affected area of the patient O.

The patient O can be placed on the top board 30.

The table-top driving device 31 has a mechanism that, controlled by the controller 32, moves the table-top 30 up and down along the y-axis direction as well as backward and forward along the z-axis direction. The rotation portion 25 has an opening in a central portion. The patient O placed on the table-top 30 of the opening space is inserted into the opening.

The controller 32 includes a CPU (central processing unit) and a memory. The controller 32 controls the X-ray detector 23, the DAS 24, the high voltage power supply 26, the limiter driving device 27, the rotation driving device 28, the injector 29, and the table-top driving device 31 to perform scanning.

The image processing apparatus 12 of the X-ray CT apparatus 1 is computer-based and can communicate with a network N such as a backbone LAN (local area network) in a hospital. The image processing apparatus 12 is generally composed of basic hardware such as a CPU 41, a main memory 42, an image memory 43, an HDD (hard disc drive) 44, an input device 45, and a display device 46. The CPU 41 is connected to each of the hardware components constituting the image processing apparatus 12 via buses as common signal transmission lines. The image processing apparatus 12 may also include a storage medium drive 47.

The CPU 41 is a control device constructed as an integrated circuit (LSI), which is an electronic circuit produced on a semiconductor is housed in a package with multiple terminals. If an instruction is input by an operator such as a physician operating the input device 45, the CPU 41 executes a program stored in the main memory 42. Alternatively, the CPU 41 loads a program stored in the HDD 44, a program transferred from the network N and installed in the HDD 44, or a program read out from a storage medium mounted on the storage medium drive 47 and installed in the HDD 44, into the main memory 42 to execute such a program.

The main memory 42 is a storage device including an ROM (read only memory), an RAM (random access memory) and the like. The main memory 42 is used to store an IPL (initial program loading), a BIOS (basic input/output system), and data. Also, the main memory 42 is used as working memory for the CPU 41 and used to temporarily store data.

The image memory 43 is a storage device in which generated contrast volume data and simple volume data are stored.

The HDD 44 is a storage device containing undetachable metal disks on which a magnetic substance is applied or evaporated. The HDD 44 is a storage device in which programs installed in the image processing apparatus 12 (including an application program as well as an OS (operating system)) and data are stored. Also, the OS may be allowed to provide a GUI (graphical user interface) that makes heavy use of graphics for displaying information to the operator so that the operator can perform basic operations through the input device 45.

The input device 45 is a pointing device that can be operated by the operator and sends input signals according to an operation to the CPU 41.

The display device 46 includes an image synthesis circuit, VRAM (video random access memory), and a display that are not shown. The image synthesis circuit generates data obtained by superimposing character data and the like of various parameters on image data. The VRAM develops the data from the image synthesis circuit into image data to be displayed on the display. The display is composed of a liquid crystal display, a CRT (cathode ray tube), or the like, and sequentially displays items of the display image data as display images.

A storage medium is detachably mounted on the storage medium drive 47. The storage medium drive 47 reads out data (including a program) recorded on a storage medium, onto the bus. Also, the storage medium drive 47 writes data supplied via the bus into a storage medium. Such a storage medium can provide so-called packaged software.

The image processing apparatus 12 performs correction processing (preprocessing) such as logarithmic transformation processing and sensitivity correction on raw data input from the DAS 24 of the scanner 11 to generate projection data. Also, the image processing apparatus 12 performs scattered radiation removing processing on the preprocessed projection data. The image processing apparatus 12 removes scattered radiation on the basis of values of projection data within an X-ray irradiated area. The image processing apparatus 12 performs scattered radiation correction by subtracting scattered radiation from target projection data. The scattered radiation is estimated by values of the target projection data or projection data adjacent thereto. The image processing apparatus 12 reconstructs the corrected projection data to generate contrast CT image data and simple CT image data and store both the data.

Figure 2:
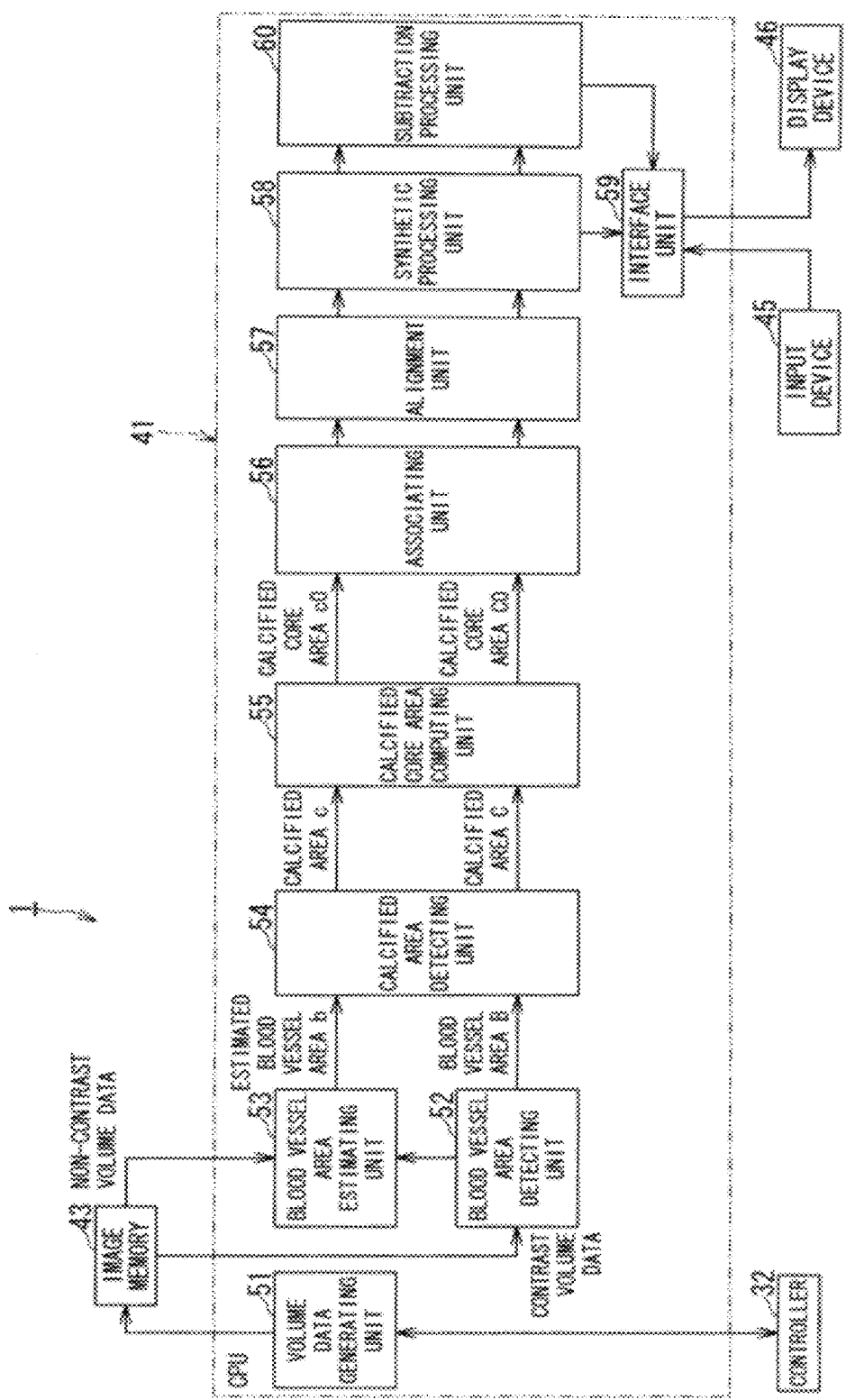
FIG. 2 is a block diagram illustrating functions of the X-ray CT apparatus according to the present embodiment.

FIG. 2 is a block diagram illustrating functions of the X-ray CT apparatus 1 according to the present embodiment. In the present embodiment, a calcified area will be described as an example of a group of pixels having a high CT value with halation (a high CT value area).

The CPU 41 of the image processing apparatus 12 executes programs, whereby the X-ray CT apparatus 1 functions as a volume data generating unit 51, a blood vessel area detecting unit 52, a blood vessel area estimating unit 53, a calcified area detecting unit 54, a calcified core area computing unit 55, an associating unit 56, an alignment unit 57, a synthetic processing unit 58, an interface unit 59, and a subtraction processing unit 60, as shown in FIG. 2. It should be noted that all or a part of the components 51 to 60 of the X-ray CT apparatus 1 may be included in the X-ray CT apparatus 1 as hardware.

The volume data generating unit 51 controls an operation of the scanner 11 by the controller 32 to generate simple CT image data on the basis of projection data of a region with beating in the patient O, the data being obtained by scanning performed before injection of a contrast medium and generate simple volume data on the basis of the simple CT image data corresponding to a plurality of cross-sections. Also, the volume data generating unit 51 controls an operation of the scanner 11 by the controller 32 to generate contrast CT image data on the basis of projection data of the region with beating in the patient O, the data being obtained by scanning performed after the injection of the contrast medium and generate contrast volume data on the basis of the contrast CT image data corresponding to a plurality of cross-sections. The generated simple and contrast volume data are stored in the image memory 43.

The blood vessel area detecting unit 52 detects a blood vessel area (contrast medium area) B on the basis of the contrast volume data obtained from the image memory 43. The blood vessel area detecting unit 52 detects the blood vessel area B from the contrast volume data on the basis of segmentation of the blood vessel area and blood vessel tracing.

Figure 3:
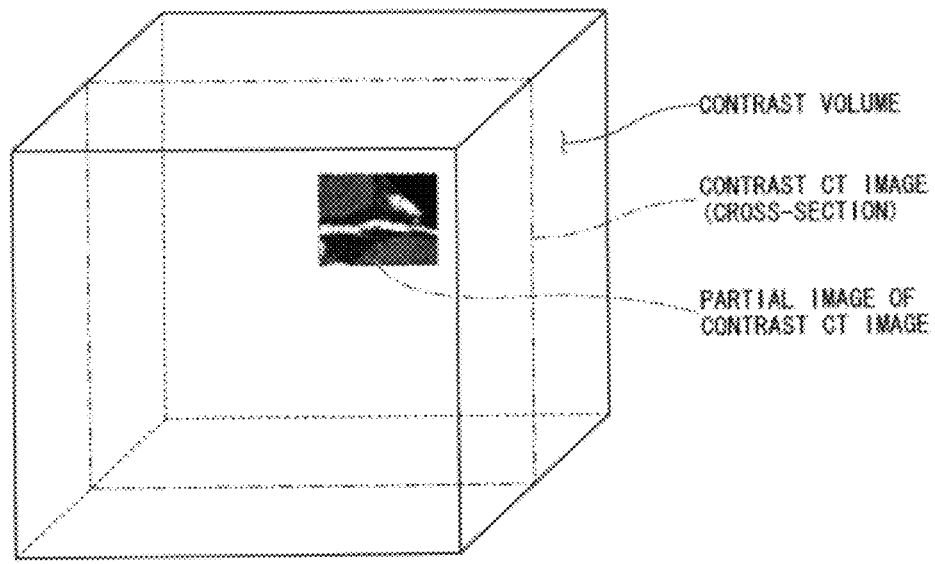
FIG. 3 is a diagram illustrating a contrast CT image (partial image) formed by contrast CT image data corresponding to a required cross-section of contrast volume data.
Figure 4:
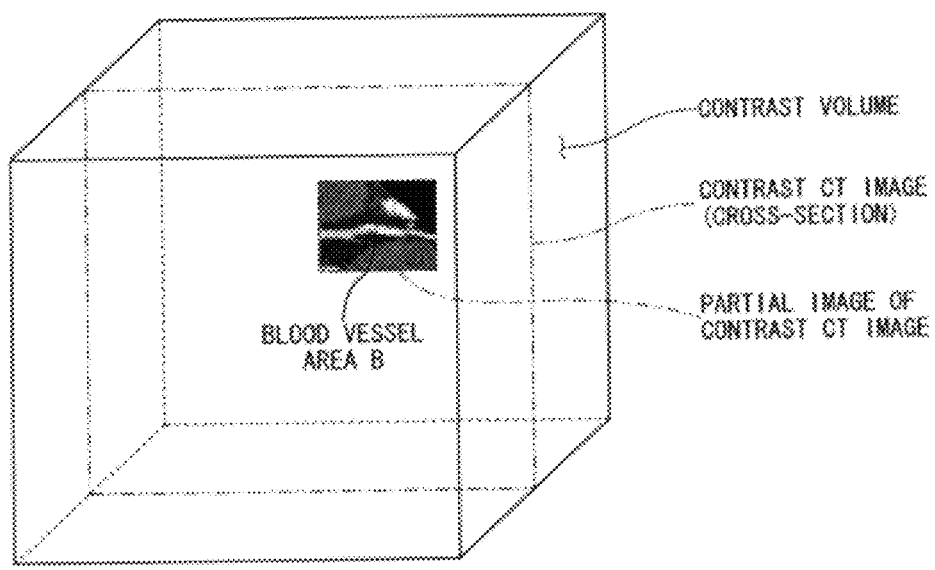
FIG. 4 is a diagram illustrating a blood vessel area detected on the contrast CT image (partial image) illustrated in FIG. 3.

FIG. 3 is a diagram illustrating a contrast CT image (partial image) formed by contrast CT image data corresponding to a required cross-section of contrast volume data. FIG. 4 is a diagram illustrating a blood vessel area detected on the contrast CT image (partial image) illustrated in FIG. 3.

FIG. 3 illustrates a contrast volume formed by the contrast volume data and the contrast CT image (partial image) formed by the contrast CT image data corresponding to the required cross-section of the contrast volume data. FIG. 4 illustrates the contrast volume and the contrast CT image (partial image) illustrated in FIG. 3, and the blood vessel area B on the contrast CT image.

The blood vessel area estimating unit 53 illustrated in FIG. 2 aligns entire contrast volume data in which a blood vessel area and a calcified area are detected by the blood vessel area detecting unit 52 with entire simple volume data obtained from the image memory 43 and having a same cardiac phase as that of the contrast volume data in which the blood vessel area is detected by the blood vessel area detecting unit 52, and aligns entire internal organs. The blood vessel area estimating unit 53 also estimates a blood vessel area b in the simple volume data by the blood vessel area B in the contrast volume data. The blood vessel area estimating unit 53 coarsely aligns the contrast volume data with the simple volume data, thereby determining a part of the simple volume data corresponding to the blood vessel area B in the contrast volume data as the estimated blood vessel area b.

The calcified area detecting unit 54 detects a calcified area C on the basis of contrast volume data obtained from the image memory 43. For example, the calcified area detecting unit 54 detects a calcified area (an object area) C around the blood vessel area B detected by the blood vessel area detecting unit 52 (area of interest) on the basis of the contrast volume data, that is, a calcified area C appearing within a predetermined range from the blood vessel area B.

Figure 5:
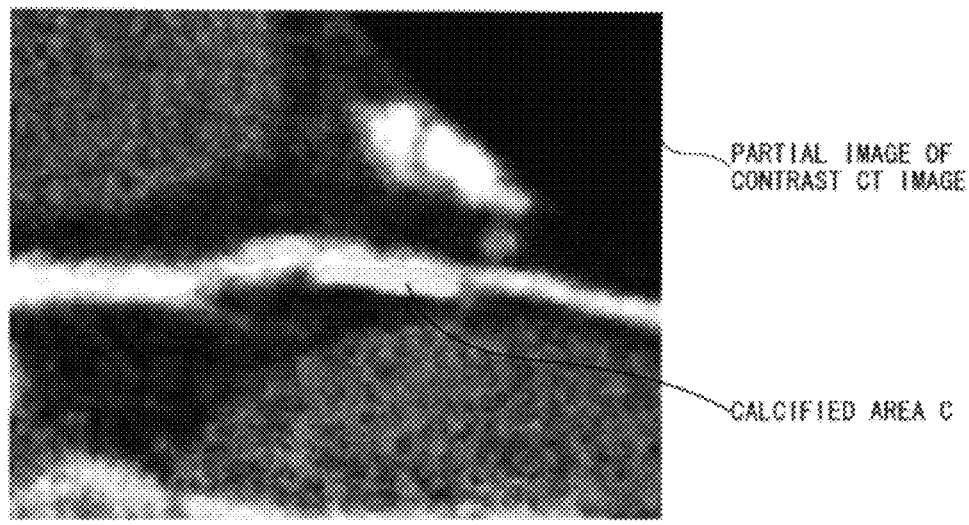
FIG. 5 is a diagram illustrating the contrast CT image (partial image) illustrated in FIG. 3 and a detected calcified area.
Figure 6:
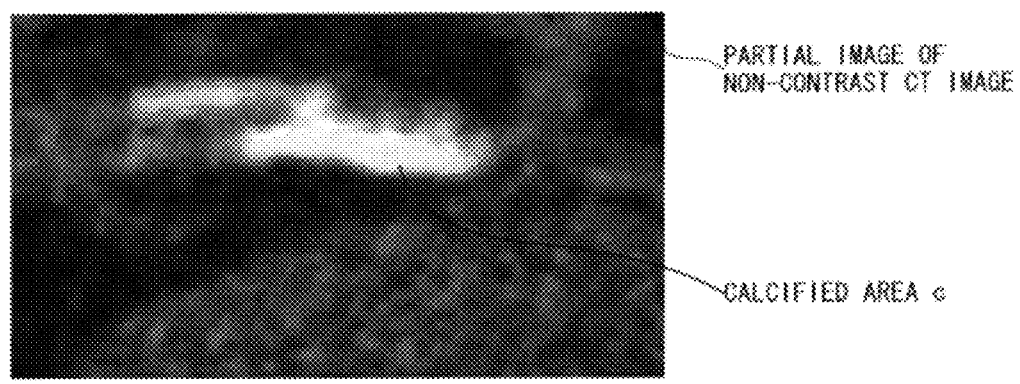
FIG. 6 is a diagram illustrating a simple CT image (partial image) formed by simple CT image data corresponding to the required cross-section of the simple volume data, and a estimated calcified area.

Also, the calcified area detecting unit 54 detects a calcified area c on the basis of the simple volume data. For example, the calcified area detecting unit 54 detects a calcified area c around the blood vessel area b estimated by the blood vessel area estimating unit 53 on the basis of the simple volume data obtained from the image memory 43, that is, a calcified area c appearing within a predetermined range from the estimated blood vessel area b. The calcified area detecting unit 54 detects calcified areas C and c appearing around the blood vessel area B and the estimated blood vessel area b, respectively, by threshold processing with a threshold being a fixed value or a value obtained by multiplying a maximum value in the area by a coefficient according to the value. FIG. 5 illustrates the calcified area C detected on the basis of the contrast CT image (partial image) illustrated in FIG. 3. FIG. 6 illustrates the calcified area c estimated on the basis of the simple CT image (partial image) formed by the simple CT image data corresponding to the required cross-section of the simple volume data. The calcified area detecting unit 54 provides the simple volume data with the calcified area c as information used for alignment.

In the calcified area C in the contrast volume data and the calcified area c of the simple volume data, blurring occurs due to cardiac movements and a cardiac phase difference (respiratory movements). Thus, in processing described below, a calcified core area C0 in the calcified area C is computed on the basis of a distribution of CT values of the contrast volume data. Also, a calcified core area c0 in the calcified area c is computed on the basis of a distribution of CT values of the simple volume data.

The calcified core area computing unit 55 computes the calcified core area C0 on the basis of the distribution of the CT values of the calcified area C detected by the calcified area detecting unit 54. Also, the calcified core area computing unit 55 computes the calcified core area c0 on the basis of the distribution of the CT values of the calcified area c detected by the calcified area detecting unit 54. The calcified core area computing unit 55 may determine a correction function (the spread of the foot on a distribution of CT values) of the calcified core area C0 of the calcified area C from each of an average value and a standard deviation of CT values of pixels corresponding to the calcified area C, or by deconvolution using a gamma function or an MTF (modulation transfer function) of a known reconstructing filter. The calcified core area computing unit 55 computes a calcified core area $C0[n, m]$ of an m-th (m=1, 2, ..., M) in a calcified area $C[n]$ of an n-th (n=1, 2, ..., N). The calcified core area c0 of the calcified area c may also be computed similarly to the calcified area C.

Figure 7:
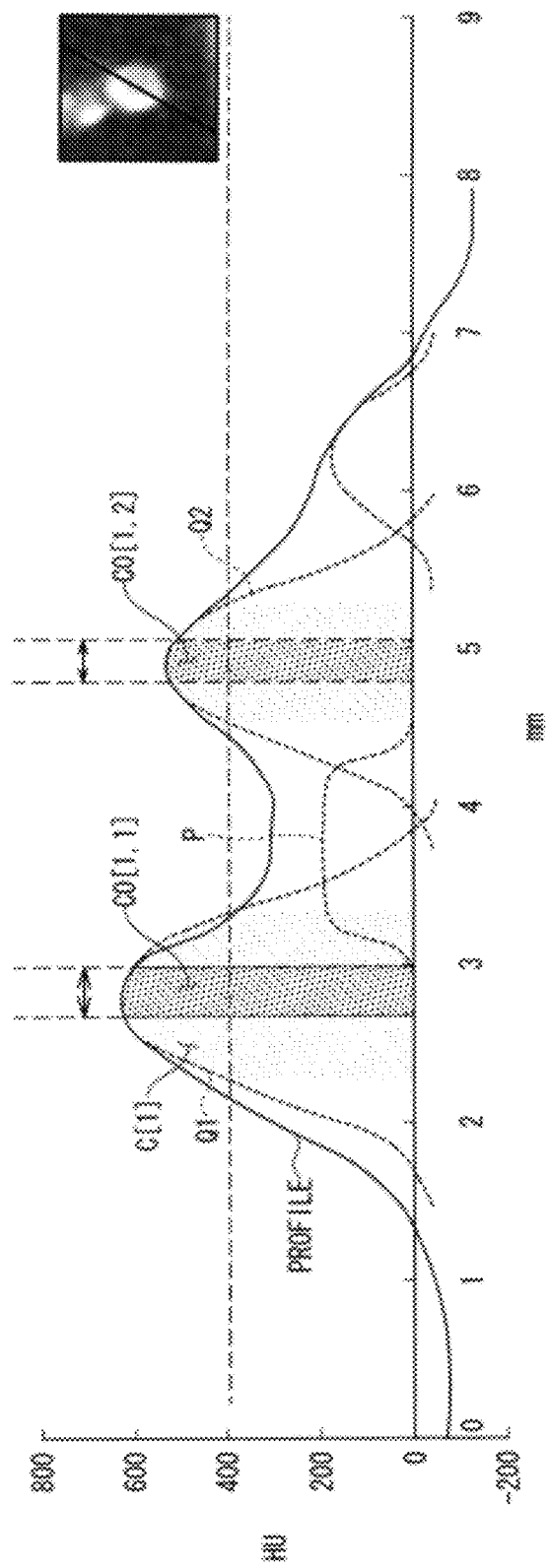
FIG. 7 is a graph representing a profile of CT values on a cross-section of the contrast volume data.

FIG. 7 is a graph representing a profile of CT values on a cross-section of the contrast volume data.

A vertical axis in FIG. 7 indicates CT values of the contrast volume data and a horizontal axis indicates coordinates on a line in an upper right image.

FIG. 7 illustrates a profile of CT values on a cross-section of contrast volume data, a first calcified area $C[1]$, and a first calcified core area $C0[1,1]$ and a second calcified core area $C0[1,2]$ of the first calcified area $C[1]$ in a one-dimensional manner. Also, FIG. 7 illustrates a correction function P of the blood vessel area B, a correction function Q1 of the calcified core area $C0[1,1]$, and a correction function Q2 of the calcified core area $C0[1,2]$, based on a profile of CT values on a cross-section of the contrast volume data.

In FIG. 7, the calcified core area computing unit 55 uses a profile of CT values on a cross-section of the contrast volume data as an example of a distribution of CT values of the contrast volume data to compute a calcified core area on the basis of the profile of the CT values. However, the distribution of the CT values of the contrast volume data is not limited to a profile of CT values on a cross-section of the contrast volume data. For example, the distribution of the CT values of the contrast volume data may be contour data based on the contrast volume data.

FIGS. 8A to 8E are diagrams illustrating a relationship between a calcified area $C[n]$ and a calcified core area $C0[n, m]$ of the calcified area $C[n]$.

Figure 8A:
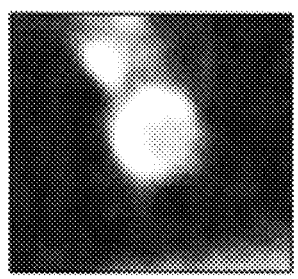
FIGS. 8A to 8E are diagrams illustrating a relationship between a calcified area and a calcified core area of the calcified area.
Figure 8C:
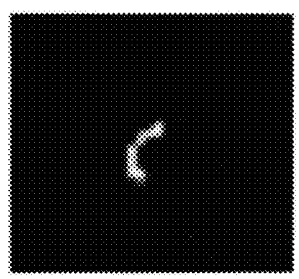
Figure 8B:
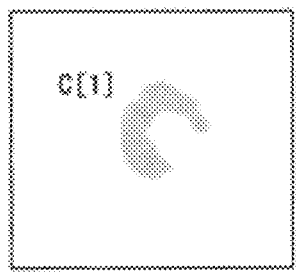
Figure 8D:
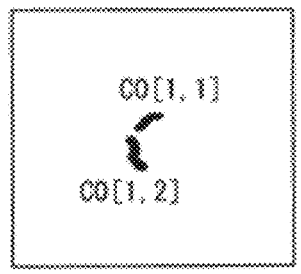
Figure 8E:
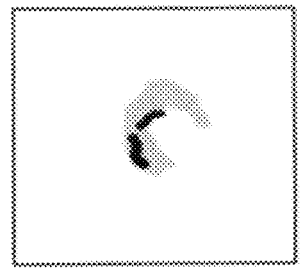

FIG. 8A illustrates a contrast CT image (partial image) based on contrast volume data. FIG. 8B illustrates a calcified area $C[1]$ detected from FIG. 8A. FIG. 8C illustrates a calcified core area in the contrast CT image (partial image) based on the contrast volume data. FIG. 8D illustrates calcified core areas $C0[1,1]$ and $C0[1,2]$ in the calcified area $C[1]$, the core areas being computed from FIG. 8A. FIG. 8E illustrates the calcified area $C[1]$ in FIG. 8B on which the calcified core areas $C0[1,1]$ and $C0[1,2]$ in FIG. 8D are superimposed.

The associating unit 56 illustrated in FIG. 2 associates the calcified core area C0 in the contrast volume data computed by the calcified core area computing unit 55, with the calcified core area c0 of the simple volume data. For associating, the associating unit 56 sequentially numbers the calcified core areas C0 from a calcified core area C0 (calcified core area c0) of origin to a peripheral calcified core area C0 (calcified core area c0) of the blood vessel area B in the contrast volume data (the estimated blood vessel area b of the simple volume data).

The alignment unit 57 linearly or non-linearly aligns contrast volume data with simple volume data on the basis of the associating performed by the associating unit 56. For example, the alignment unit 57 performs linear/non-linear alignment by a method that uses an amount of normalized mutual information as similarity, a method that uses anatomical information, and the like. The alignment unit 57 can align entire volume data, or only indicated target structures with each other. For example, the alignment unit 57 may target only parts of contrast volume data and simple volume data.

Figure 9:
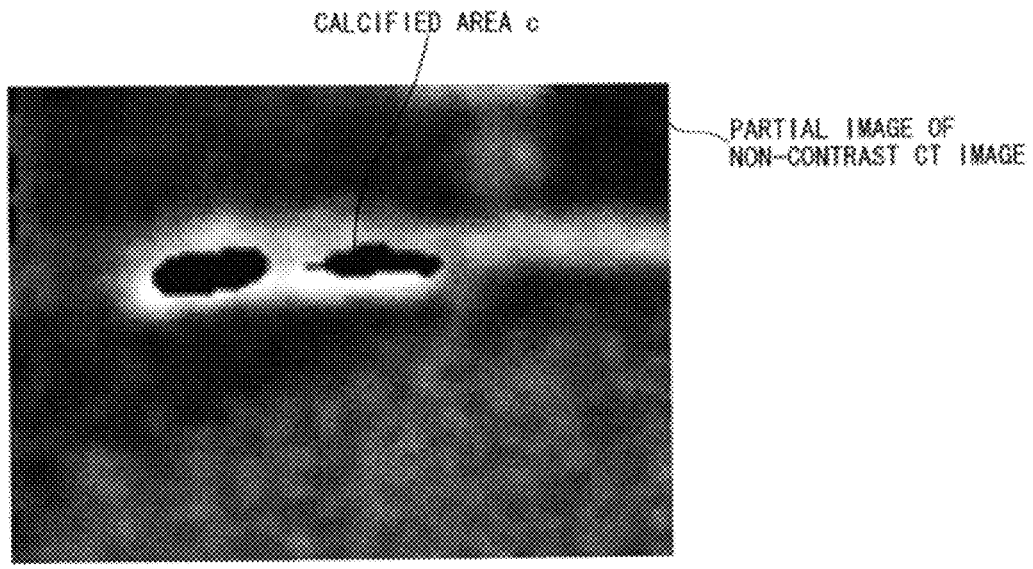
FIG. 9 is a diagram illustrating a simple CT image (partial image) based on simple volume data, which has yet to undergo the superimposing processing.
Figure 10:
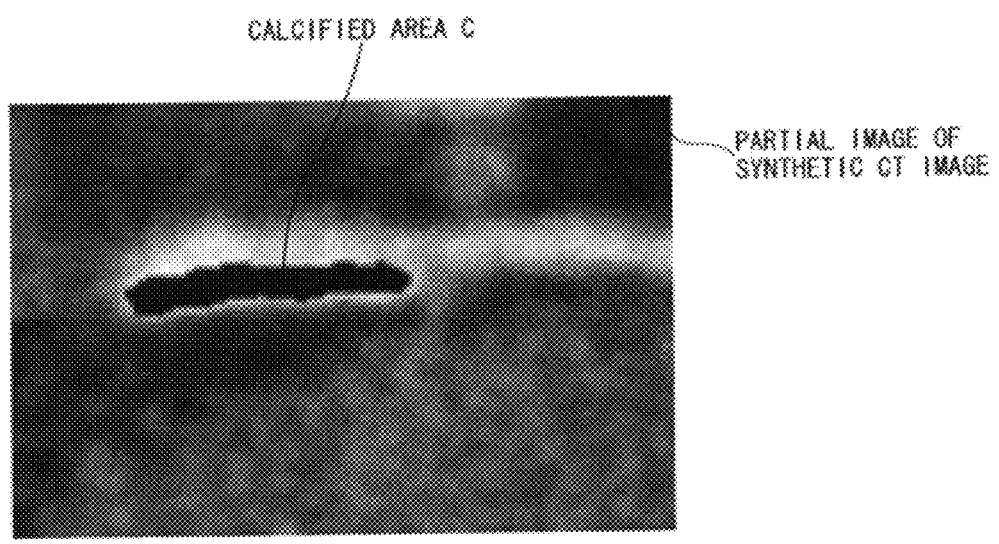
FIG. 10 is a diagram illustrating a superimposed CT image (partial image) based on superimposed volume data, which has undergone the superimposing processing.

The synthetic processing unit 58 generates superimposed volume data by superimposing the calcified area C on the simple volume data on the basis of the contrast volume data and the simple volume data aligned with each other by the alignment unit 57. FIG. 9 illustrates a simple CT image (partial image) based on simple volume data, which has yet to undergo the superimposing processing. FIG. 10 illustrates a superimposed CT image (partial image) based on superimposed volume data, which has undergone the superimposing processing.

The interface unit 59 is a user interface that can change the superimposed calcified area C through the input device 45, on a screen displaying a superimposed CT image via the display device 46. The superimposed volume data is displayed on the display device 46 through the interface unit 59.

Also, the synthetic processing unit 58 generates synthesized volume data by performing additive synthesis or multiplication synthesis of the simple volume data and the calcified area C on the basis of the contrast volume data and the simple volume data aligned with each other by the alignment unit 57.

The subtraction processing unit 60 generates subtraction volume data by performing subtraction processing between the contrast volume data and the synthesized volume data generated by the synthetic processing unit 58. The subtraction volume data is displayed on the display device 46 through the interface unit 59.

Figure 11:
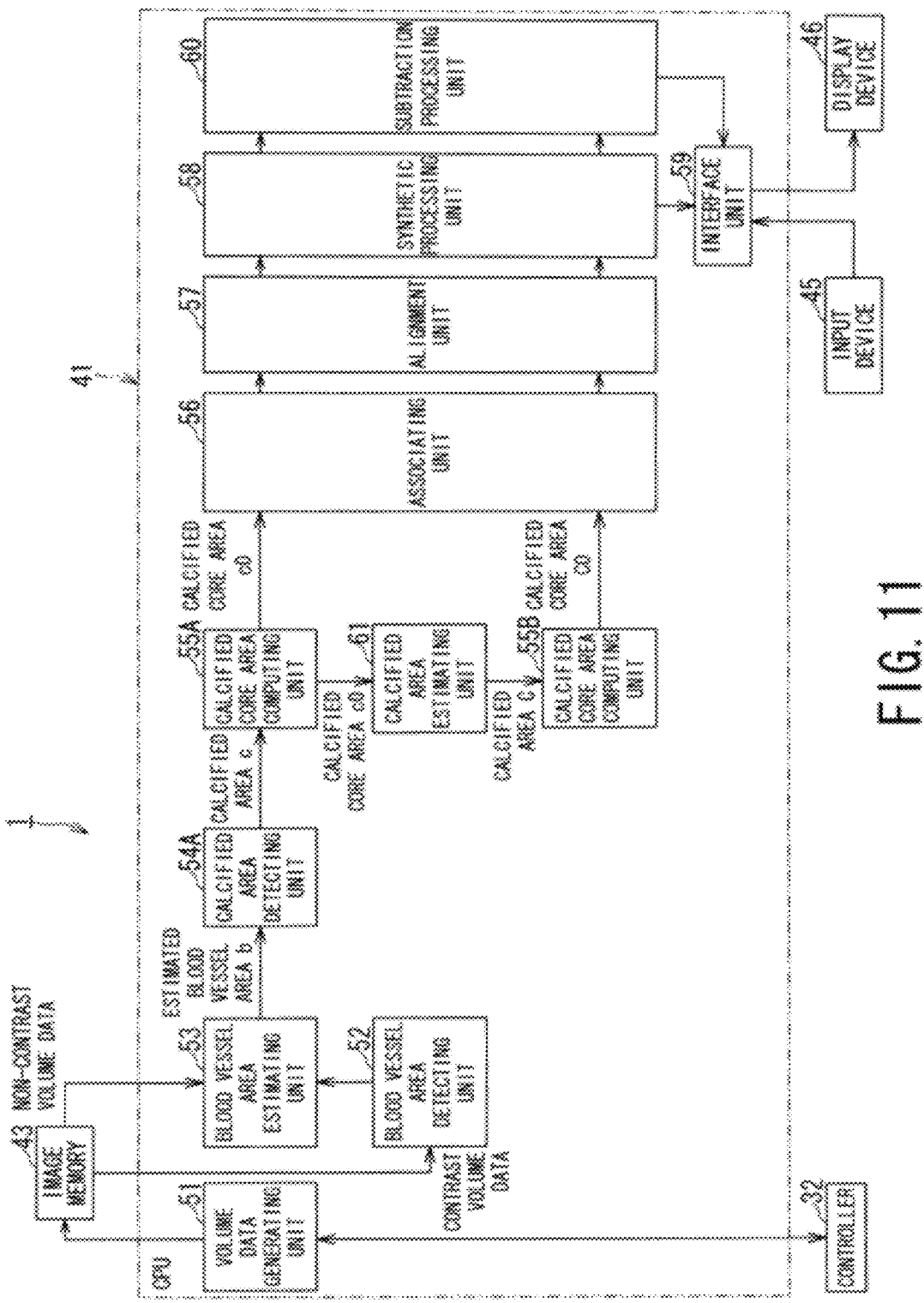
FIG. 11 is a block diagram illustrating a modified example of the functions of the X-ray CT apparatus according to the present embodiment in FIG. 2.

FIG. 11 is a block diagram illustrating a modified example of the functions of the X-ray CT apparatus 1 according to the present embodiment in FIG. 2.

The CPU 41 of the image processing apparatus 12 executes programs, whereby the X-ray CT apparatus 1 functions as a volume data generating unit 51, a blood vessel area detecting unit 52, a blood vessel area estimating unit 53, a calcified area detecting unit 54A, a calcified core area computing unit 55A, a calcified area estimating unit 61, a calcified core area computing unit 55B, an associating unit 56, an alignment unit 57, a synthetic processing unit 58, an interface unit 59, a subtraction processing unit 60, and a calcified area estimating unit 61, as shown in FIG. 11. It should be noted that all or a part of the components 51 to 61 of the X-ray CT apparatus 1 may be included in the X-ray CT apparatus 1 as hardware.

Similarly to some function of the calcified area detecting unit 54, the calcified area detecting unit 54A detects a calcified area c around a blood vessel area b estimated by the blood vessel area estimating unit 53, that is, a calcified area c appearing within a predetermined range from the estimated blood vessel area b.

Similarly to some function of the calcified core area computing unit 55, the calcified core area computing unit 55A computes a calcified core area c0 on the basis of the calcified area c detected by the calcified area detecting unit 54A.

The calcified area estimating unit 61 aligns entire contrast volume data in which a blood vessel area is detected by the blood vessel area detecting unit 52 with entire simple volume data in which the calcified core area c0 is computed by the calcified core area computing unit 55A, and aligns entire internal organs. The calcified area estimating unit 61 also estimates a calcified area C in the contrast volume data by the calcified core area c0.

If a highly concentrated contrast medium is injected into the patient O, as compared with the calcified area c in the simple volume data, burring of the calcified area C in the contrast volume data is significant. The burring of the calcified area C in the contrast volume data is caused by burring of the contrast medium. For this reason, the calcified area estimating unit 61 estimates the calcified area C in the contrast volume data on the basis of the calcified core area c0 in the simple volume data, the area c0 being computed by the calcified core area computing unit 55A.

Similarly to some function of the calcified core area computing unit 55, the calcified core area computing unit 55B computes the calcified core area C0 on the basis of the calcified area C estimated by the calcified area estimating unit 61.

The associating unit 56 associates the calcified core area C0 in the contrast volume data computed by the calcified core area computing unit 55B, with the calcified core area c0 in the simple volume data computed by the calcified core area computing unit 55A.

In FIG. 11, the same reference numerals are used for denoting the same functions as those in FIG. 2, and redundant descriptions thereof are omitted.

The calcified area estimating unit 61 may estimate pixel values or correction values thereof (hereinafter, referred to as the "pixel values or the like") of a calcified area C in the contrast volume data on the basis of a calcified area c in non-contrast volume data. The calcified area C is a corresponding area of the calcified area c. The calcified area estimating unit 61 may directly determine the pixel values of the calcified area C. Also, the calcified area estimating unit 61 may determine correction values for reducing a false image appearing after subtraction processing and then correct the directly-determined pixel values of the calcified area C. In this case, when the subtraction processing unit 60 generates subtraction volume data by performing subtraction processing between the non-contrast volume data and the contrast volume data, pixel values of an area in the subtraction volume data and corresponding to the calcified area C are determined by using the pixel values of the estimated calcified area C.

It should be noted that calcification causing a high CT value area on a CT image has been described as an example in relation to the X-ray CT apparatus 1 of the present embodiment, but this case is not restrictive. Examples of other factors that cause a high CT value area on a CT image include a metal medical instrument such as a stent or a bolt. In this case, the calcified core area computing units 55, 55A, and 55B will compute material substance of the medical instrument.

The X-ray CT apparatus 1 according to the present embodiment aligns contrast volume data with simple volume data on the basis of calcified core areas C0 and c0. Then, the X-ray CT apparatus 1 according to the present embodiment superimposes the calcified area C on the simple volume data to generate superimposed volume data and performs displaying on the basis of the superimposed volume data. Thus, according to the X-ray CT apparatus 1 of the present embodiment, it can be visually observed whether the calcified area C causes blurring.

Alternatively, the X-ray CT apparatus 1 according to the present embodiment aligns contrast volume data with simple volume data on the basis of calcified core areas C0 and c0. Then, the X-ray CT apparatus 1 of the present embodiment generates synthesized volume data by additive synthesis of the simple volume data and the calcified area C, and performs subtraction processing between the contrast volume data and the synthesized volume data to generate subtraction volume data. Thus, according to the X-ray CT apparatus 1 of the present embodiment, since the calcified area C, which has a high CT value, can be canceled, there may be provided an image suitable for evaluating a lumen of a blood vessel.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image processing apparatus comprising:
    a contrast side obtaining unit configured to, on the basis of contrast data obtained after contrast radiography is performed, obtain a contrast area and a high computed tomography (CT) value area around the contrast area;
    an estimating unit configured to, on the basis of the contrast data and aligned non-contrast data obtained without contrast, estimate a contrast area in the non-contrast data and corresponding to the obtained contrast area;
    a simple side obtaining unit configured to obtain a high CT value area around the estimated contrast area on the basis of the non-contrast data;
    a core area computing unit configured to, on the basis of a distribution of CT values of the contrast data, compute a core area included in the high CT value area of the contrast data and to, on the basis of a distribution of CT values of the non-contrast data, compute a core area included in the high CT value area of the non-contrast data;
    a synthesizing unit configured to, on the basis of the core area of the contrast data and the core area of the non-contrast data, align the contrast data with the non-contrast data and generate superimposed data by superimposing the high CT value area of the contrast data on the non-contrast data; and
    a display control unit configured to display the superimposed data on a display device.

2. The image processing apparatus according to claim 1, wherein
    the core area computing unit is configured to compute the core area of the contrast data on the basis of a profile of CT values on a cross-section in the contrast data and compute the core area of the non-contrast data on the basis of a profile of CT values on a cross-section in the non-contrast data.

3. The image processing apparatus according to claim 1, further comprising
    a changing unit configured to, on a display screen of the superimposed data, change the superimposed high CT value area.

4. The image processing apparatus according to claim 1, wherein
    the core area computing unit is configured to perform deconvolution on the high CT value area with a gamma function or an MTF (modulation transfer function) of a reconstructing filter as a transfer function and compute the core area by using a correction function having a minimal difference from the profile.

5. The image processing apparatus according to claim 1, wherein
    the synthesizing unit is configured to partially align the core area of the contrast data with the core area of the non-contrast data to generate partial superimposed data.

6. The image processing apparatus according to claim 1, wherein
    the synthesizing unit is configured to linearly/non-linearly align the contrast data with the non-contrast data.

7. The image processing apparatus according to claim 1, further comprising
    an associating unit configured to associate a required core area of the plurality of core areas in the contrast data with a required core area of the plurality of core areas in the non-contrast data.

8. The image processing apparatus according to claim 7, wherein
    the synthesizing unit is configured to align the required core areas with each other, associated by the associating unit.

9. The image processing apparatus according to claim 1, wherein
    the contrast side obtaining unit is configured to obtain the high CT value area in the contrast data on the basis of the core area of the non-contrast data computed by the core area computing unit.

10. The image processing apparatus according to claim 1, further comprising a subtracting unit, wherein
    the synthesizing unit is configured to align the contrast data with the non-contrast data on the basis of the core area of the contrast data and the core area of the non-contrast data, and perform additive synthesis or multiplication synthesis of the high CT value areas of the non-contrast data and the contrast data to generate synthetic data, and
    the subtracting unit is configured to perform subtraction processing between the contrast data and the synthetic data to generate subtraction data.

11. An image processing apparatus comprising:
    an extracting unit configured to, on the basis of a blood vessel area of non-contrast image data, extract an object area in which an object exists;
    an estimating unit configured to, on the basis of the object area in the non-contrast image data, estimate pixel values or correction values of the pixel values of a corresponding area of the object area, in contrast image data; and
    a subtracting unit configured to perform subtraction processing between the non-contrast image data and the contrast image data to generate subtraction image data and to determine pixel values of an area corresponding to the corresponding area, in the subtraction image data, by using the estimated pixel values or correction values of the corresponding area.

12. The image processing apparatus according to claim 11, wherein
    the object area is a high CT value area.

13. The image processing apparatus according to claim 11, further comprising:
    a first core area computing unit configured to, on the basis of the non-contrast image data, determine a core area of the extracted object area;
    a second core area computing unit configured to, on the basis of the contrast image data, determine a core area of the estimated corresponding area; and an alignment unit configured to, on the basis of the first and second core areas determined by the first and the second core area computing units, align the non-contrast image data with the contrast image data, wherein the subtracting unit is configured to, on the basis of an alignment result from the alignment unit, generate the subtraction image data.

14. An X-ray CT apparatus comprising:

a scanning unit configured to generate contrast data obtained after contrast radiography and non-contrast data obtained without contrast by controlling an X-ray source and an X-ray detector;

a contrast side obtaining unit configured to, on the basis of the contrast data, obtain a contrast area and a high CT value area around the contrast area;

an estimating unit configured to, on the basis of the contrast data and aligned non-contrast data, estimate a contrast area in the non-contrast data and corresponding to the obtained contrast area;

a simple side obtaining unit configured to obtain a high CT value area around the estimated contrast area on the basis of the non-contrast data;

a core area computing unit configured to, on the basis of a distribution of CT values of the contrast data, compute a core area included in the high CT value area of the contrast data and to, on the basis of a distribution of CT values of the non-contrast data, compute a core area included in the high CT value area of the non-contrast data;

a synthesizing unit configured to, on the basis of the core area of the contrast data and the core area of the non-contrast data, align the contrast data with the non-contrast data and generate superimposed data by superimposing the high CT value area of the contrast data on the non-contrast data; and a display control unit configured to display the superimposed data on a display device.

15. The X-ray CT apparatus according to claim 14, wherein the core area computing unit is configured to compute the core area of the contrast data on the basis of a profile of CT values on a cross-section in the contrast data and compute the core area of the non-contrast data on the basis of a profile of CT values on a cross-section in the non-contrast data.

16. The X-ray CT apparatus according to claim 14, further comprising a subtracting unit, wherein the synthesizing unit is configured to align the contrast data with the non-contrast data on the basis of the core area of the contrast data and the core area of the non-contrast data, and perform additive synthesis or multiplication synthesis of the high CT value areas of the non-contrast data and the contrast data to generate synthetic data, and the subtracting unit is configured to perform subtraction processing between the contrast data and the synthetic data to generate subtraction data.

17. An image processing method comprising:

obtaining a contrast area and a high CT value area around the contrast area on the basis of contrast data stored in a storage and obtained after contrast radiography is performed;

estimating a contrast area in non-contrast data stored in a storage and obtained without contrast, and corresponding to the obtained contrast area on the basis of the contrast data and aligned non-contrast data;

obtaining a high CT value area around the estimated contrast area on the basis of the non-contrast data;

computing a core area included in the high CT value area of the contrast data on the basis of a distribution of CT values of the contrast data, and computing a core area included in the high CT value area of the non-contrast data on the basis of a distribution of CT values of the non-contrast data;

aligning the contrast data with the non-contrast data on the basis of the core area of the contrast data and the core area of the non-contrast data, and generating superimposed data by superimposing the high CT value area of the contrast data on the non-contrast data; and displaying the superimposed data on a display device.

18. The image processing method according to claim 17, wherein computing the core area of the contrast data on the basis of a profile of CT values on a cross-section in the contrast data and computing the core area of the non-contrast data on the basis of a profile of CT values on a cross-section in the non-contrast data.

19. The image processing method according to claim 17, wherein aligning the contrast data with the non-contrast data on the basis of the core area of the contrast data and the core area of the non-contrast data, and performing additive synthesis or multiplication synthesis of the high CT value areas of the non-contrast data and the contrast data to generate synthetic data, and performing subtraction processing between the contrast data and the synthetic data to generate subtraction data.

* * * * *